United States Patent [19]

Singer et al.

[11] Patent Number: 5,180,553
[45] Date of Patent: Jan. 19, 1993

[54] PROCESS TO DESTROY BACTERIA

[76] Inventors: Joachim Singer; Jurgen Singer, both of Ziegeleistrasse 2-6, 6901 Mauer, Fed. Rep. of Germany

[21] Appl. No.: 666,507

[22] Filed: Mar. 7, 1991

Related U.S. Application Data

[63] Continuation of Ser. No. 435,000, Nov. 12, 1989, abandoned.

[30] Foreign Application Priority Data

Nov. 12, 1988 [DE] Fed. Rep. of Germany ....... 3838448

[51] Int. Cl.$^5$ ................................. A61L 2/20
[52] U.S. Cl. ...................... 422/28; 422/37; 422/40; 426/335; 426/422
[58] Field of Search ............... 422/10, 28, 37, 40; 426/335, 422

[56] References Cited

U.S. PATENT DOCUMENTS

| | | | |
|---|---|---|---|
| 3,364,068 | 1/1968 | Stern | 422/37 |
| 3,576,594 | 4/1971 | Knetemann et al. | 422/37 |
| 3,624,200 | 11/1971 | Meflett | |
| 3,947,568 | 3/1976 | Bates et al. | |
| 4,021,197 | 5/1977 | Brooks | 422/28 |
| 4,048,343 | 9/1977 | Levine | 436/330.2 |
| 4,325,296 | 4/1982 | Ukai et al. | 422/28 |

FOREIGN PATENT DOCUMENTS 3015813 10/1981 Fed. Rep. of Germany.

OTHER PUBLICATIONS

Dr. Hans Kübler, "*Kosmetische Aerosole*", Aerosol Report, vol. 27, No. 10/88, pp. 465-472.
"Hawley's Condensed Chemical Dictionary", Eleventh Edition, Revised by N. Irving Sax and Richard J. Lewis, Sr., Van Nostrand Reinhold Company, New York, 1987, pp. 177, 220, 414.
"CRC Handbook of Chemistry and Physics", 60th Edition, Robert C. Weast, Ph.D. Editor, CRC Press, Inc., Boca Raton, Florida, 1979-1980, pp. E-29, E-31.

Primary Examiner—Robert J. Warden
Assistant Examiner—Timothy M. McMahon
Attorney, Agent, or Firm—Wegner, Cantor, Mueller & Player

[57] ABSTRACT

What is described is a process to destroy cells, cellular products, infectious particles and similar pathogens on solid objects as well as in preparations of various components in order to preserve these preparations. For this, the solid objects or preparations are placed or filled into pressure container equipped with a valve, and that the contents of the container are subsequently filled with gas.

14 Claims, 4 Drawing Sheets

PROCESS TO DESTROY BACTERIA

This application is a continuation of U.S. application Ser. No. 07/435,000, filed Nov. 12, 1989, now abandoned.

DESCRIPTION OF THE INVENTION

The invention concerns a process to destroy cell, cellular products, infectious particles and similar pathogens on solid objects, as well as in preparations consisting of various substances and to preserve theses preparations, in particular cosmetic and pharmaceutical products.

Harmful cells, cellular products, fungi and similar pathogens can grow on contaminated solid objects as well as in chemical products, for example cosmetics and drugs. The contaminated products themselves can then become harmful and cause illness. In general, cosmetic products and medicinal products are good cultural media for the growth of bacteria, fungi and similar organisms, so that it is vital that these products be protected. The danger or increased contamination occurs everywhere where cleansing, care or conditioning cosmetics as well as where medicinal products in the form of salves, pastes, creams or emulsions are stored in tubes, dispensers, jars, bottles and similar packages from which smaller amounts of these products are removed over long periods of time.

Therefore, it cannot be disputed that all these products need to be protected against toxic decomposition products, because such products can lead to sometimes severe damage to the health of the user.

It is generally accepted that this type of protection can only be provided by the addition of chemical preservatives. At the present state of the art, many chemical products exist, which fulfil this task.

It is, however, also recognized that the use of preservatives is not without consequences for the user, in particular as they can trigger allergic reactions. It is for this reason that regulations governing the use of preservatives exist. An allergic reaction to preservatives in humans can, however, be triggered by the most varied causes, so that even the most conscientious and careful testing and approval criteria cannot guarantee the safety of a preservative. In addition to this, the problem arises that the multitude of possible contaminations produced by pathogens and microorganisms each acting in very different ways, also requires the use of a variety of preservatives, so that the number of these soon becomes too large to control.

Finally, it must be noted that a large number of the preservatives used merely prevent the growth of cells which are already present in the product such as those, for example, which are introduced during filling, and do not achieve a complete destruction of the cells.

It is the object of the invention to produce a process of the above-named type, which will not only prevent cellular growth but also simply and economically keep the solid objects and the cosmetic and medicinal products free of cells, while avoiding any residual toxic effect.

This object is achieved by a process of the above-named type by placing or pouring the solid objects or the preparations in a gas-pressure container equipped with a valve and subsequently filling the container with gas.

Further embodiments of the process are characterized in the sub-claims.

Figure 1:
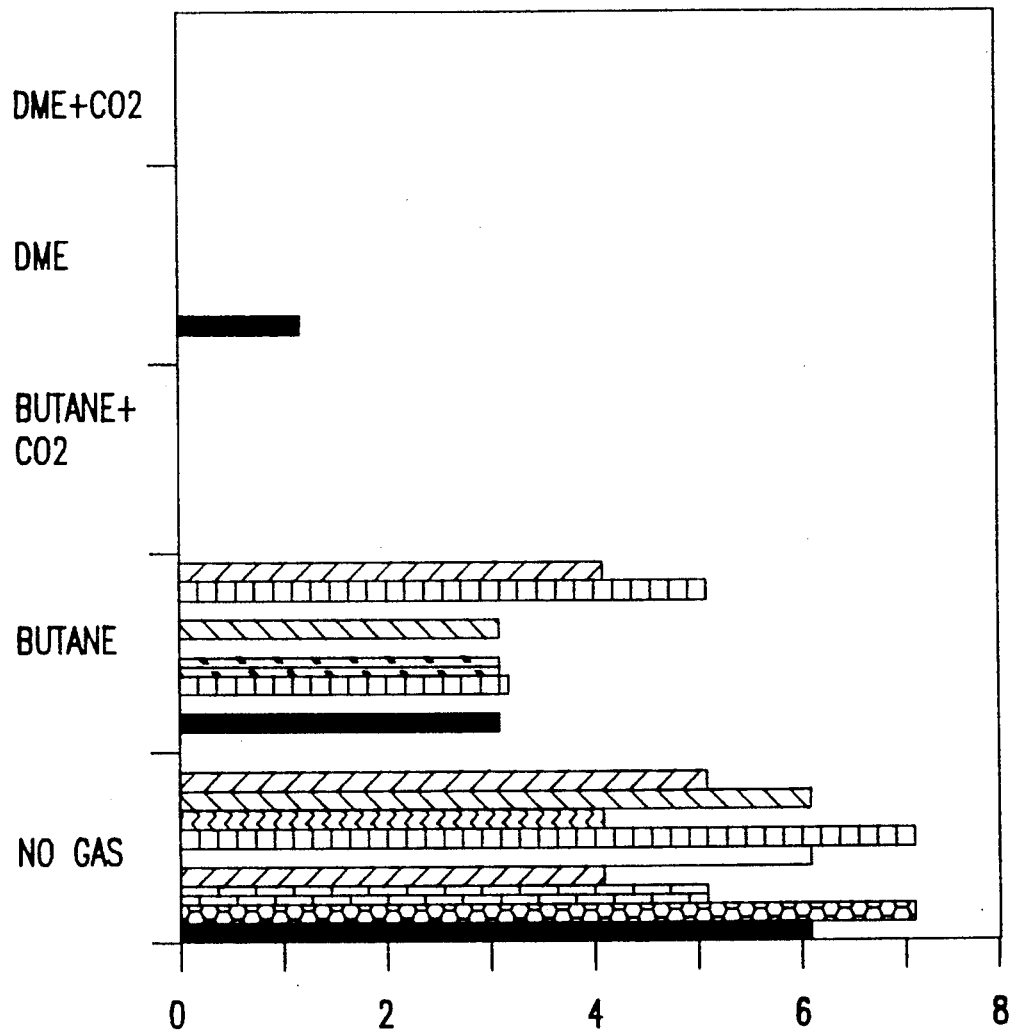
FIGS. 1 to 4 show graphically the data of tables 3 and 4.

Against the general opinion of the technical community, it was found that for the above-named areas of application, the use of chemical preservatives could be avoided. Instead of the usual pots, tubes, jars and similar containers, the cosmetic or medicinal products are filled into pressure cans together with the conventional propellants, and then a gas or gas mixture is added. Surprisingly, it was found that samples which had been prepared in this manner ten years ago were still in perfect condition when released and exhibited no signs of decomposition. The preparation used for this consisted of material which was subject to rapid decomposition, namely fresh eggs. It was shown that even cells which are particularly difficult to destroy could successfully be fought.

It was also discovered that by employing the process in accordance with the invention, solid objects could also be made bacteria-free and thus be easily sterilized. This discovery is of particular importance to the medical sector, where the problem of contamination of instruments and equipment is always of importance. Before each use, these must be absolutely sterile, that is, free of any live cells capable of reproduction, cellular products and infectious particles. Known methods of sterilization are only adequately effective within the thermostable range. These methods employ an autoclave producing steam under a pressure of 1 bar and at 134° C. and dry heat at 180° C. There are obvious limitations in the applications employed for the thermoinstable range, that is, ethylene oxide, formaldehyde or radiation sterilization, primarily because of material incompatibility, but also because of the human toxicity of the gases employed.

Using the process in accordance with the invention, solid objects can be easily sterilized.

The invention is described in greater detail by several experiments.

As a base test, the first experiments were carried out with products which easily spoil.

Hot water was added in the usual manner to the fat phase 70° to 80° C.:

| % by weight | Material |
| --- | --- |
| 3.0 | Paraffin oil |
| 8.0 | Anhydrous lanolin |
| 3.0 | Emulsion wax |
| 10.0 | Sweet almond oil |
| 0.2 | Vitamin A palmitate |
| 49.6 | Demineralized water, 80° C. |

An emulsion consisting of the following and produced under sold conditions was stirred into to the above cream, once it had cooled to 30° to 40° C.

| 10.0 | Fresh, whole egg |
| --- | --- |
| 10.0 | Sunflower oil |
| 0.2 | Ascorbic acid |
| 5.0 | Sodium lactate, 50% |
| 1.0 | Perfume oil |

This mixture was then filled into glass aerosol bottles in a proportion of 68 g of mixture to 7.5 g of liquefied gas as a propellant. The liquid gas consisted of difluorodichloromethane/butane in a ratio of 3:1.

Subsequently, the final mixture of active ingredients/liquid gas was pressurized with $CO_2$ to a pressure of 10 bar—this pressure may, however, be higher. Depending on the composition of the active ingredients, this pressure rapidly decreases, so that legal limits set for pressure packs can be easily complied with.

The final mixture was examined for microorganisms by an independent research establishment, which found the following:

| Cell count: | |
|---|---|
| Bacteria | <10/g |
| Fungi | <10/g |
| Yeast | <10/g |

The results gave the impetus for further, intensive research. The purpose of this was to determine what the effect on the various cells the various combinations of liquefied gases, that is, butane, dimethyl ether, propane/butane and $CO_2$, $N_2$, $N_2O$ had.

The cream used for these experiments consisted of the following:

| g % by weight | Material |
|---|---|
| Fat phase | |
| 2.0 | Paraffin oil |
| 3.8 | Emulsion wax |
| 1.0 | Anhydrous lanolin |
| 1.0 | Bee's wax |
| 20.0 | Sunflower oil |
| Aqueous phase | |
| 70.2 | Demineralized water |
| 2.0 | Glycerin |
| 100.0% | |

As is normally the case for emulsions, the fat and aqueous phases were heated to 80° C. and then stirred together.

After cooling to approx. 40° C., the emulsion was homogenized.

All other experiments were performed on samples of this cream mixture. In order to answer the question of to what extent the process actually destroys microorganisms rather than merely acting as a preservative, 50 g of the cream was filled into several 100 ml cans and contaminated with various cells. The cans were subsequently sealed against the entry of air and shaken in order to provide an even distribution. Gas was then added to the cans. 3.5 g each of liquefied gas, namely butane, dimethyl ether as well as, in some cases, propane/butane and mixed gases, were used. The other gases, namely $CO_2$, $N_2$, $N_2O$ were added at a pressure of 12 bar. After shaking, this pressure rapidly dropped in the containers to which $CO_2$ and $N_2O$ had been added.

In parallel to this, pure cell cultures in a growth medium were filled into 100 ml cans, and gas was added in the same way as to the creams. For this, the individual types of cells were mixed with one another.

The following Tables 1 and 2 contain the results of the first experiments described as "Creme" and "Medium". Three different types of cells which are common to both humans themselves and the environment in general were employed:

| 1. *Staphylococcus aureus* | Small, round, ball-shaped bacteria with a high resistance to a dry environment. |
|---|---|
| 2. *Candida albicans*: | Thick-walled, gram-positive, capsulated yeasts, which do not form spores and are round to oval in shape. |
| 3. *Pseudomonas aeruginosa*: | Rod-shaped bacteria with a high resistance to a moist environment. |

Gas addition was carried out in the following manner:
Addition of only compressed air at 10 bar;
Addition of only $N_2$ at 12 bar;
Addition of only $N_2O$ at 12 bar;
A combination of butane and $N_2$
A combination of butane and $N_2O$
A combination of DME* and $N_2$
A combination of DME and $N_2O$
* DME = Dimethyl ether The results of all these experiments were unsatisfactory or showed that these agents were not successful in reducing cells.

The results of the experiments with the effective gases and gas mixtures are shown in Table 1.

The gas mixture consisted of a combination of butane and dichlorodifluoromethane in a ratio of 1:3.

The numerical values are logarithmic values, that is, 5.0 represents $10^5$ cells per gram of cream, etc.

Contamination took on Nov. 14, 1988, with $10^5$ test cells per gram of cream and $10^7$ test cells per milliter of medium. The various substances were examined for microorganisms on Nov. 19, 1988, Nov. 28, 1988, Dec. 27, 1988 and Jul. 27, 1989.

TABLE 1

| | | CREAM | | | | | |
|---|---|---|---|---|---|---|---|
| | | BUTANE | | GAS MIXTURE | | DME | |
| Cell type | No gas | alone | +$CO^2$ | alone | +$CO^2$ | alone | +$CO^2$ |
| 11/19/88 | | | | | | | |
| Staph. aureus | 5.0 | <2 | <2 | <2 | <2 | <1 | <1 |
| Pseud. aerug. | 5.0 | <2 | <2 | <2 | <2 | <1 | <1 |
| Cand. albic. | 4.0 | <2 | <2 | <2 | <2 | <1 | <1 |
| 11/28/88 | | | | Values unchanged | | | |
| 27/12/88 | | | | Values unchanged | | | |
| 07/25/88 | | | | | | | |
| Staph. aureus | >5.0 | <2 | <2 | <2 | <2 | <1 | <1 |
| Pseud. aerug. | >5.0 | <2 | 4 | 6 | 3.0 | <1 | <1 |
| Cand. albic. | >6.0 | <2 | <2 | <2 | <2 | <1 | <1 |

TABLE 2

| Test date/ | | MEDIUM | | | | | |
|---|---|---|---|---|---|---|---|
| | | BUTANE | | GAS MIXTURE | | DME | |
| Cell type | No gas | alone | $-CO_2$ | alone | $+CO_2$ | alone | $+CO_2$ |
| 11/19/88 | | | | | | | |
| Staph. aureus | 7.0 | | | | | | |
| Pseud. aerug. | 7.0 | \} The qualitative test was positive in 1 ml | | | | | |
| Cand. albic. | 6.0 | of medium for all cultures. | | | | | |
| 11/28/88 | | | | | | | |
| Staph. aureus | >7.0 | | | | | | |
| Pseud. aerug. | >7.0 | 5.0 | 5.0 | 5.0 | 5.0 | 1.0 | 1.0 |
| Cand. albic. | >6.0 | | | | | | |
| 12/27/88 | | | | | | | |
| Staph. aureus | >8.0 | | | | | | |
| Pseud. aerug. | >8.0 | >6.0 | 4.0 | 5.0 | 3.0 | <1.0 | <1.0 |
| Cand. albic. | >7.0 | | | | | | |
| 07/25/89 | | | | | | | |
| Staph. aureus | >7.0 | 5.0 | <2.0 | <2.0 | <2.0 | <1.0 | <1.0 |
| Pseud. aerug. | >7.0 | 5.0 | <2.0 | 5.0 | 7.0 | <1.0 | <1.0 |
| Cand. albic. | >7.0 | 7.0 | <2.0 | 6.0 | <2.0 | 3.0 | <1.0 |

The tables show that, with certain gas combinations, not only is an excellent bacteriostatic effect achieved, but also a cell mortality action. This can be seen particularly in Table 2, "Medium", where the combination of DME and $CO_2$ was particularly effective.

Despite the high initial cell numbers in the control cans which received no gas treatment, these nonetheless exhibited strong cellular growth during the eight month test period. This shows that the cream itself had no cell destroying properties.

The results shown above were confirmed in a further series of tests, in which creams and media were contaminated with various cell concentrations between $10^7$ and $10^3$ cells per gram of cream or milliliter of medium.

Contamination took place on Jan. 16, 1989, and the mixtures were examined for bacterial content on Jan. 20, 1989, Jan. 25, 1989 and Jul. 17, 1989. The results are summarized in Table 3 and FIG. 1.

TABLE 3

| Test date/ | | CREAM | | | |
|---|---|---|---|---|---|
| | | BUTANE | | DME | |
| Cell type | No gas | alone | $+CO_2$ | alone | $+CO_2$ |
| 01/20/89 | | | | | |
| Staph. aureus | 6.0 | 2.0 | n.f. | 1.0 | n.f. |

TABLE 3-continued

| Test date/ | | CREAM | | | |
|---|---|---|---|---|---|
| | | BUTANE | | DME | |
| Cell type | No gas | alone | $+CO_2$ | alone | $+CO_2$ |
| Pseud. aerug. | 7.0 | n.f. | n.f. | n.f. | n.f. |
| Cand. albic. | 5.0 | 3.0 | n.f. | n.f. | n.f. |
| 01/25/89 | | | | | |
| Staph. aureus | 4.0 | 3.0 | n.f. | n.f. | n.f. |
| Pseud. aerug. | 6.0 | n.f. | n.f. | n.f. | n.f. |
| Cand. albic. | 7.0 | 3.0 | n.f. | n.f. | n.f. |
| 07/17/89 | | | | | |
| Staph. aureus | 4.0 | n.f. | n.f. | n.f. | n.f. |
| Pseud. aerug. | 6.0 | 5.0 | n.f. | n.f. | n.f. |
| Cand. albic. | 5.0 | 4.0 | n.f. | n.f. | n.f. | n.f. = none found

Here too, the results with the medium showed a difference to those with the cream. Keeping the initial cell numbers in mind ($10^3$ to $10^8$), Table 4 "Medium" and the graphs which go with them (FIG. 2, 3 and 4), clearly show that dimethyl ether (DME) alone and as a gas mixture with $CO_2$ produces a complete cell mortality which begins within 24 hours after the addition of the gas and—even at an initial cell concentration of $10^8$ cells per ml—remains in effect throughout the entire 6 month test period.

TABLE 4

| Test date/ | Initial cell | MEDIUM | | | | | |
|---|---|---|---|---|---|---|---|
| | | | BUTANE | | DME | | |
| Cell type | number | No gas | alone | $+CO_2$ | alone | $+CO_2$ | |
| 01/20/89 | | | | | | | |
| All 3 cell types | 8.0 | 8.0 | 3.0 | 4.0 | n.f. | n.f. | |
| (FIG. 2) | 7.0 | 7.0 | | | | | |
| | 6.0 | 6.0 | | | | | |
| | 5.0 | 5.0 | \} Under measurable levels | | | | |
| | 4.0 | 4.0 | | | | | |
| | 3.0 | 3.0 | | | | | |
| 01/25/89 | | | | | | | |
| All 3 cell types | 8.0 | 9.0 | 5.0 | 4.0 | n.f. | n.f. | |
| (FIG. 3) | 7.0 | 9.0 | 5.0 | 3.0 | n.f. | n.f. | |
| | 6.0 | 9.0 | 3.0 | 3.0 | n.f. | n.f. | |
| | 5.0 | 9.0 | 2.0 | 2.0 | n.f. | n.f. | |
| | 4.0 | 9.0 | 4.0 | 2.0 | n.f. | n.f. | |
| | 3.0 | 9.0 | 3.0 | 1.0 | n.f. | n.f. | |
| 07/17/89 | | | | | | | |
| All 3 cell types | 8.0 | 8.0 | n.f. | n.f. | n.f. | n.f. | |
| (FIG. 4) | 7.0 | 8.0 | 5.0 | 2.0 | n.f. | n.f. | |
| | 6.0 | 8.0 | 5.0 | n.f. | n.f. | n.f. | |
| | 5.0 | 8.0 | n.f. | n.f. | n.f. | n.f. | |
| | 4.0 | 8.0 | n.f. | 2.0 | n.f. | n.f. | |

TABLE 4-continued

| Test date/ Cell type | Initial cell number | MEDIUM | | | | |
|---|---|---|---|---|---|---|
| | | No gas | BUTANE alone | $-CO^2$ | DME alone | $+CO^2$ |
| | 3.0 | 8.0 | n.f. | n.f. | n.f. | n.f. | n.f. = none found

Figure 2:
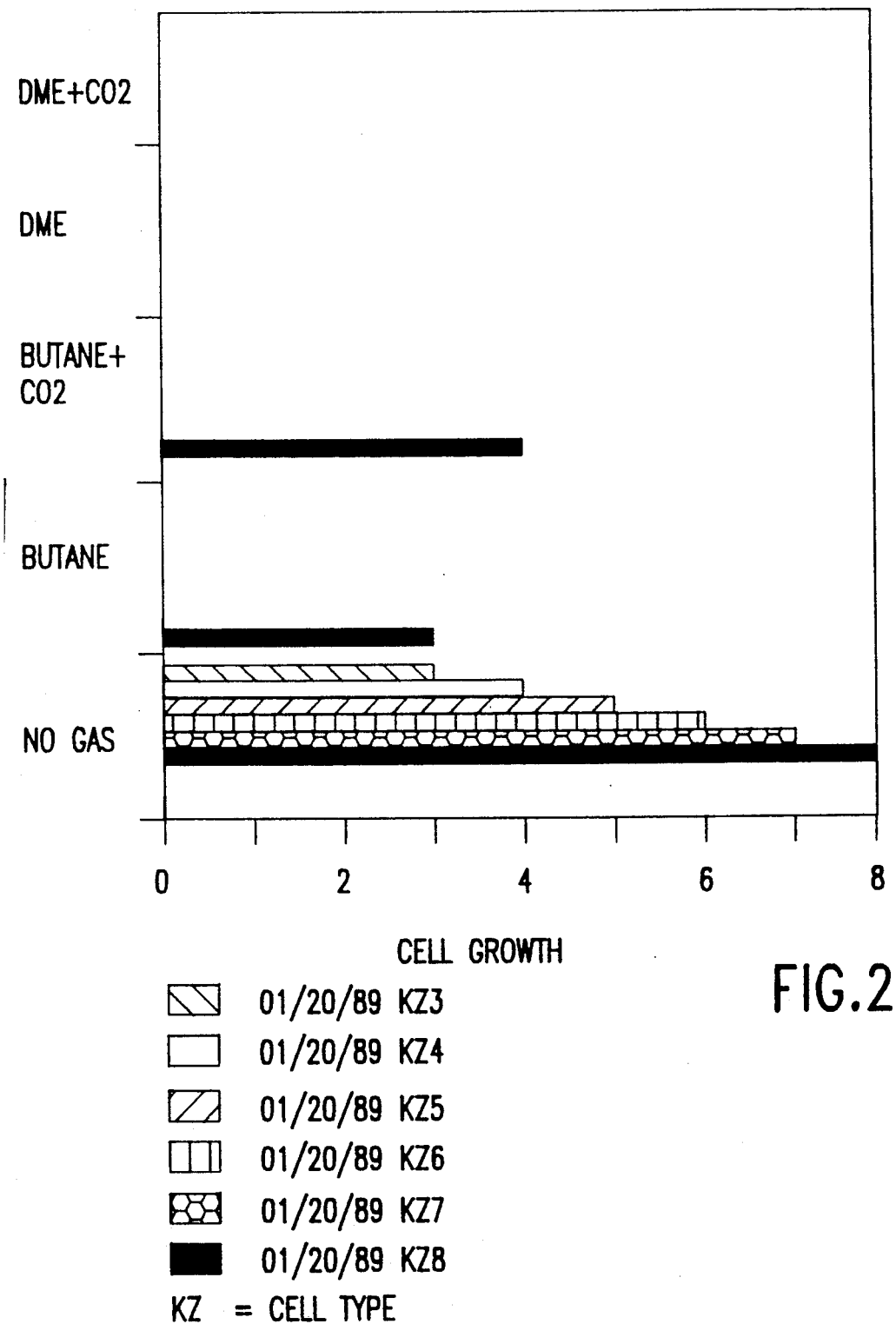
Figure 3:
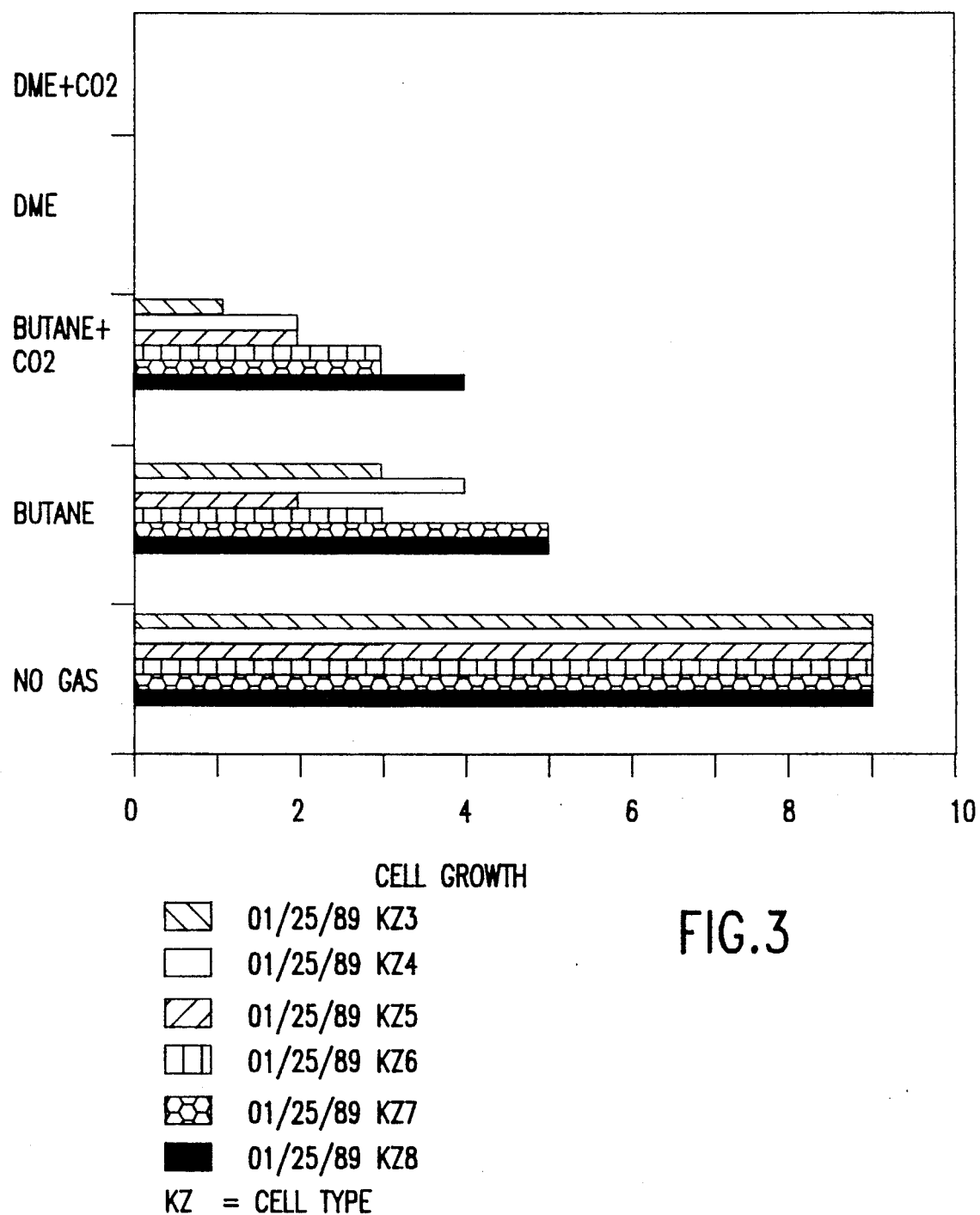
Figure 4:
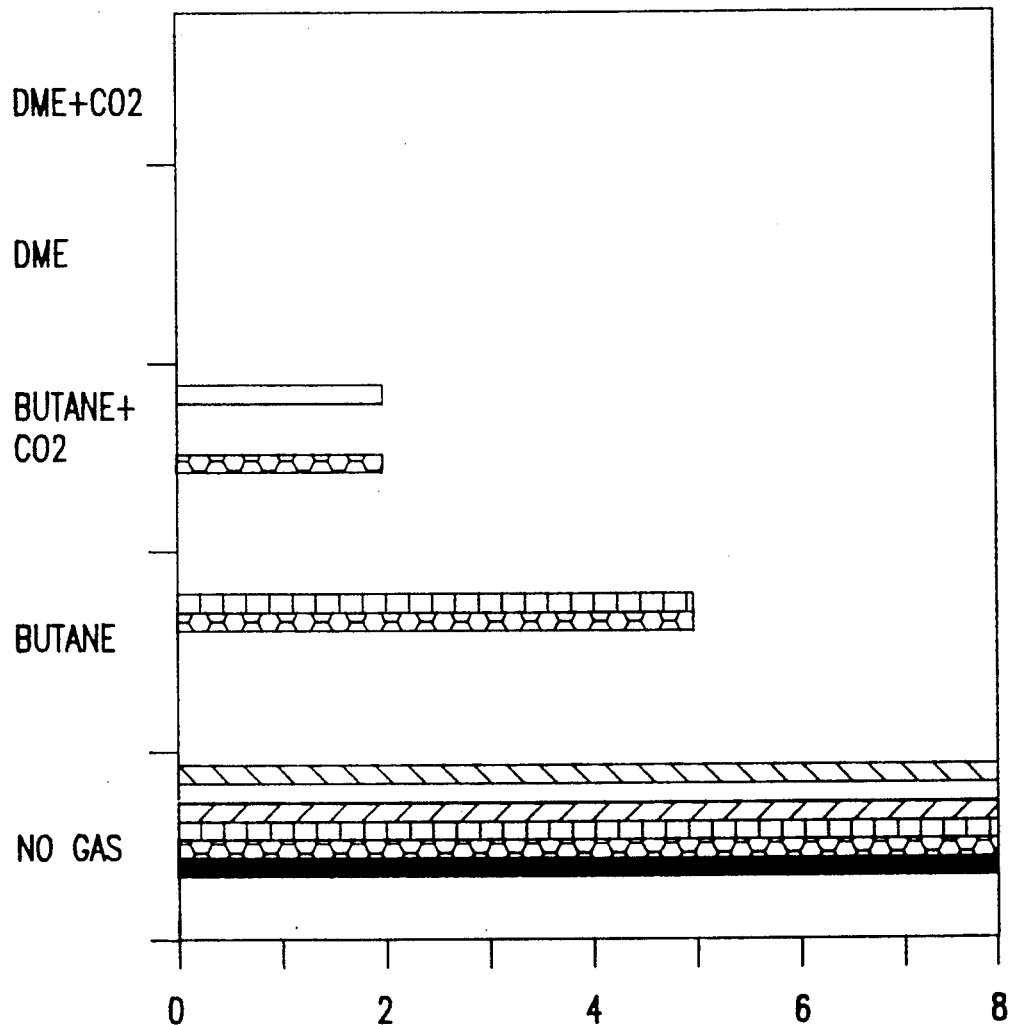

FIG. 2, 3 and 4 show the results particularly well.

In order to further test the effectiveness of the system, the types of cells tested were expanded, and some particularly resistant cell types were used. In addition to the three types of cells named above, the following were also employed:

| | |
|---|---|
| Aspergillus niger: | Black, rod fungus; |
| Mycobacterium terrae: | Belonging to the group of tubercular bacteria, high environmental resistance; |
| Bacillus subtilis: | Widely dispersed rods with a rapid reproductive rate and the capacity to form spores, that is, resistant survival forms; |
| Bacillus sterothermophilus: | Also extremely resistant because of their ability to form spores; used as indicator cells for autoclave testing |

Even for these types of cells, which in some cases are extremely resistant, dimethyl ether or dimethyl ether $+CO_2$ could, in some instances, completely destroy all colonies, but, at the very least, produce a reduction by 5 to 6 logarithmic steps.

Butane or butane $+CO_2$ proved to be noticeably less effective.

The results clearly show that, by employing the above-named process, it is possible to produce and maintain cosmetic and medicinal products which are free of cells without the use of chemical preservatives.

Further studies tested the use of this process to remove cells—that is, to sterilize—solid bodies, in particular medical instruments and equipment.

Methodology

In the process, solid objects in pressure containers are rinsed and aerated with liquefied gas in the presence of a liquid. Tweezers and plastic disks, which had been contaminated with the bacteria listed below, were placed in pressure packs which had been deaerated with $CO_2$, and the containers were then filled with a 3.5% by volume or 7.5% by volume 0.9% saline solution. The packs were then sealed and approx. 70% of the total volume of each pack was filled with the individual liquefied gases.

The following combinations of liquefied gases were again tested:

Butane alone and in combination with $CO_2$, and
DME alone and in combination with $CO_2$.

The tweezers and plastic discs were contaminated with the following cellular solutions:

| Cell type: | Concentration in g/ml Initial cell count: |
|---|---|
| Staphylococcus aureus | $1.0 \times 10^7$ |
| Candida albicans: | $7.1 \times 10^6$ |
| Pseudomonas aeruginosa | $1.1 \times 10^8$ |
| Aspergillus niger | $3.0 \times 10^6$ |
| Bacillus subtilis | $1.3 \times 10^7$ |
| E. coli | $2.0 \times 10^8$ |

Results

In all gas combinations tested, a reduction of at least 4 logarithmic steps was found for all types of cells.

For the combination of DME+$CO_2$+3.5% by volume 0.9% NaCl, as well as DME+7.5% by volume 0.9% NaCl, no cells were found to remain after only 23 hours of exposure.

These results clearly show that the destruction of microorganisms and resistant cellular products brought about by the above-named process in creams and solutions, can also be achieved with contaminated solid objects.

The pressures used lay between 3 and 20 bar and wherein the total volume of gas added is between 5 and 20% by weight with respect to the weight of the preparation.

What is claimed is:

1. A process for preserving cosmetic, medicinal and pharmaceutical preparations by destroying cells, cellular products, infectious particles and similar pathogens contained therein, comprising filling a preparation into a pressure container equipped with a valve, and filling said pressure container with a gas compound or mixture consisting of butane, dimethylether and carbon dioxide, or butane and carbon dioxide in an amount effective to preserve the preparation.

2. A process in accordance with claim 1, wherein the amount of said gas compound or mixture added is between 5 and 20% by weight with respect to the weight of the preparation.

3. A process in accordance with claim 2, wherein said gas compound or mixture is added to the preparation to a pressure of between 3 and 20 bar.

4. A process in accordance with claim 1, wherein said gas compound or mixture is added to the preparation to a pressure of between 3 and 20 bar.

5. A process in accordance with claim 1, wherein said gas compound or mixture is dimethyl ether and carbon dioxide.

6. A process in accordance with claim 1, wherein said gas compound or mixture is butane and carbon dioxide.

7. A process in accordance with claim 1, wherein the preparation being preserved is a cosmetic preparation.

8. A process for preserving solid objects by destroying cells, cellular products, infectious particles and similar pathogens contained thereon, comprising placing a solid object in a pressure container equipped with a valve, and filling said pressure container with a gas compound or mixture consisting of butane and dichlorofluoromethane, butane and dimethylether, or butane, said gas compound or mixture alone or in combination with carbon dioxide in an amount effective to preserve the solid.

9. A process in accordance with claim 8, wherein said pressure container has been deaerated with carbon dioxide.

10. A process in accordance with claim 9, further comprising filling said pressure container with a saline solution and then sealing said pressure container before said filling with the gas compound or mixture.

11. A process in accordance with claim 9, wherein about 70% of the total volume of said pressure pack is filled with said gas compound or mixture.

12. A process in accordance with claim 8, wherein said gas compound or mixture is added to a pressure of between 3 and 20 bar.

13. A process in accordance with claim 8, wherein said gas compound or mixture is butane, dimethylether and carbon dioxide, or butane and carbon dioxide.

14. A process in accordance with claim 13, wherein said gas compound or mixture is dimethyl ether and carbon dioxide.

* * * * *